(12) United States Patent
Andersen et al.

(10) Patent No.: US 10,156,509 B2
(45) Date of Patent: Dec. 18, 2018

(54) FLAT-FIELD IMAGING SYSTEM AND METHODS OF USE

(75) Inventors: Mark Andersen, Carlsbad, CA (US); Michael C. Pallas, San Bruno, CA (US); Haopeng Wang, Arlington, VA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 674 days.

(21) Appl. No.: 14/127,152

(22) PCT Filed: Jun. 13, 2012

(86) PCT No.: PCT/US2012/042290
§ 371 (c)(1),
(2), (4) Date: Mar. 17, 2014

(87) PCT Pub. No.: WO2012/174142
PCT Pub. Date: Dec. 20, 2012

(65) Prior Publication Data
US 2014/0203169 A1     Jul. 24, 2014

Related U.S. Application Data

(60) Provisional application No. 61/498,440, filed on Jun. 17, 2011.

(51) Int. Cl.
*C12Q 1/68* (2018.01)
*C12P 19/34* (2006.01)
(Continued)

(52) U.S. Cl.
CPC ........... *G01N 15/04* (2013.01); *C12Q 1/6816* (2013.01)

(58) Field of Classification Search
CPC .................. G01N 15/04; C12Q 1/6816
(Continued)

(56) References Cited

U.S. PATENT DOCUMENTS 6,143,496 A    11/2000 Brown et al.
6,454,945 B1*   9/2002 Weigl ................ B01D 11/0492
                                                204/600

(Continued)

FOREIGN PATENT DOCUMENTS

WO    2007/024798    3/2007
WO    2007/149432   12/2007

(Continued)

OTHER PUBLICATIONS

Goon et al., "Detection and quantification of mature circulating endothelial cells using flow cytometry and immunomagnetic beads: A methodological comparison," Thrombosis and Haemostasis, Jul. 2006, vol. 96, pp. 45-52.*

(Continued)

*Primary Examiner* — Young J Kim
(74) *Attorney, Agent, or Firm* — Jones Robb, PLLC

(57) ABSTRACT

A method of aligning a plurality of targets is provided. The method includes generating a plurality of targets. A third phase includes the plurality of targets. The method further includes combining a first phase, a second phase, and the third phase in a volume. The first phase, the second phase, and the third phase are substantially immiscible, and the third phase is in fluid communication with the first phase and the second phase, and the first phase, the second phase, and the third phase are operable to be in a configuration of the third phase between the first phase and the second phase in the volume.

19 Claims, 9 Drawing Sheets

(51) Int. Cl.
*G01N 15/04* (2006.01)
*C12Q 1/6816* (2018.01)

(58) Field of Classification Search
USPC .......................................................... 348/135
See application file for complete search history.

(56) References Cited

U.S. PATENT DOCUMENTS

| | | | | |
|---|---|---|---|---|
| 7,504,265 | B2* | 3/2009 | Clague | G01N 15/1404 422/213 |
| 8,696,952 | B2* | 4/2014 | Kumacheva | A61K 9/1694 264/4.1 |
| 9,322,055 | B2 | 4/2016 | Janaway et al. | |
| 2006/0017991 | A1* | 1/2006 | Poulsen | G03B 21/60 359/20 |
| 2010/0022414 | A1* | 1/2010 | Link | B01F 3/0807 506/18 |
| 2010/0158756 | A1* | 6/2010 | Taylor | B01L 3/5027 422/69 |
| 2010/0261229 | A1 | 10/2010 | Lau et al. | |
| 2010/0261230 | A1 | 10/2010 | Liu et al. | |
| 2011/0217712 | A1* | 9/2011 | Hiddessen | C12Q 1/6846 435/6.12 |
| 2012/0258516 | A1* | 10/2012 | Schultz | B01F 3/0807 435/194 |
| 2016/0208342 | A1 | 7/2016 | Janaway et al. | |

FOREIGN PATENT DOCUMENTS

| | | |
|---|---|---|
| WO | 2010/117461 | 10/2010 |
| WO | 2012135667 A1 | 10/2012 |

OTHER PUBLICATIONS

Curcio, Mario et al., "Continuous segmented-Flow Polymerase Chain Reaction for High-Throughput Miniaturized DNA Amplification", *Anal. Chem*, vol. 75(1), American Chemical Society, 2003, 1-7.

Dorfman, Kevin D. et al., Contamination-free Continuous Flow Microfluidic Polymerase Chain Reaction for Quantitative and Clinical Applications, *Analytical Chemistry, American Chemical Society*, vol. 77, No. 11, Jun. 2005, 3700-3704.

International Search Report and Written Opinion of the ISA for International Application No. PCT/US2012/042290 dated Oct. 18, 2012.

* cited by examiner

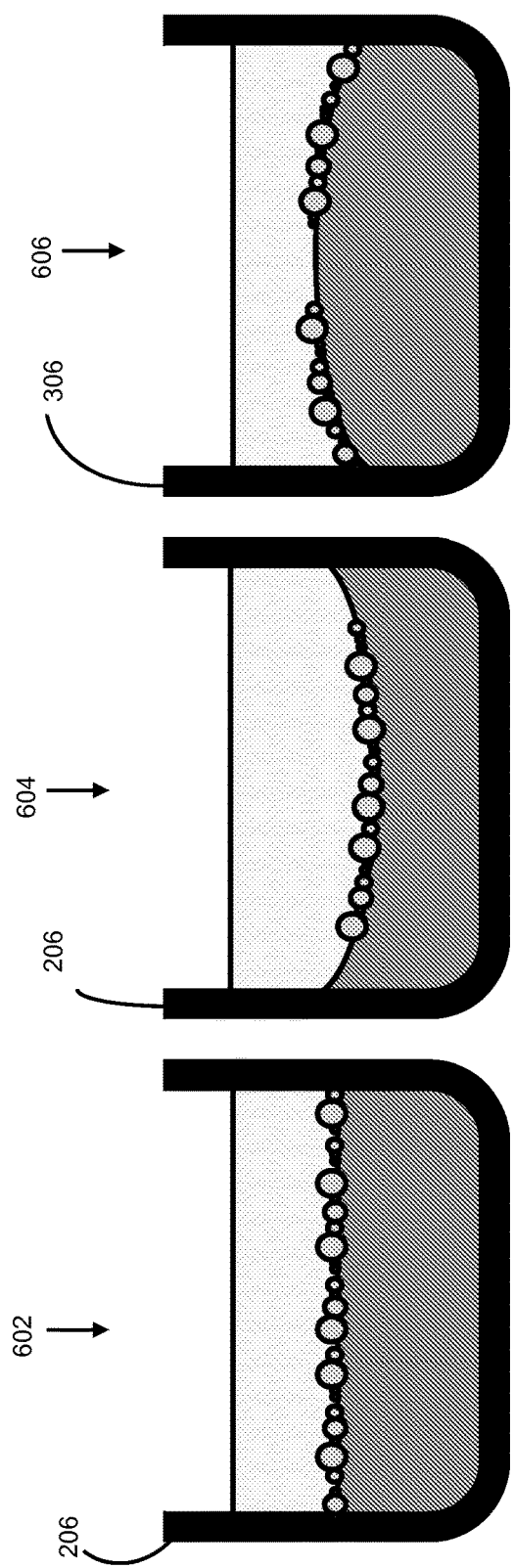

FLAT-FIELD IMAGING SYSTEM AND METHODS OF USE

CROSS-REFERENCE TO RELATED APPLICATIONS

This application is a 371 of International Application No. PCT/US2012/042290, filed Jun. 13, 2012, which claims the benefit of priority of U.S. Provisional Application Ser. No. 61/498,440, filed Jun. 17, 2011, which is incorporated herein by reference in its entirety.

BACKGROUND

Generally, there has been an increasing need for effective separation, alignment, and manipulations of colloidal and cellular suspensions or droplets and other particles based on the increasing number of systems utilizing microscale transport properties. These types of systems have significant parallelization and high throughput. Examples of applications for these systems include genetic analysis, molecular separations, sensors, imaging, printing, and surface patterning.

In one example, manipulation and positioning of the colloidal and cellular suspensions or droplets, and other particles is useful if imaging of the particles is desired. For example, the use of fluorescence detection is a ubiquitous practice in microbiology and biochemistry as well as colloidal science, biophysics and several other disciplines. Labeling cells, cellular components or individual biomolecules, or particles with molecular or colloidal fluorescent probes has enabled the visualization of several cellular metabolic and bio-molecular assembly processes. As such, methods involving fluorescent tagging, excitation, and detection may rely on methods of aligning, sorting, and manipulations.

An example of a known separation system is a fluorescence activated cell sorting (FACS) system that sorts and manipulates cells in continuous microfluidic flows. Fluorescence labeling of cells combined with traditional macroscopic FACS systems allow for the identification and separation of rare cells from concentrated suspensions, the sequestration of cells displaying desired physiological properties or metabolic states, and the parsing of large combinatorial libraries for specific information. A FACS system, however, can be complex and cumbersome. Furthermore, FACS, as well as other known alignment and sorting methods, may be improved by simplifying signal acquisition and interpretation to allow for closer to real-time feedback.

SUMMARY

In one exemplary embodiment, a method of aligning a plurality of targets is provided. The method may include generating a plurality of targets. A third phase may include the plurality of targets. The method may further include combining a first phase, a second phase, and the third phase in a volume. In some embodiments, the first phase, the second phase, and the third phase may be substantially immiscible, and the third phase may be in fluid communication with the first phase and the second phase, and the first phase, the second phase, and the third phase are operable to be in a configuration of the third phase between the first phase and the second phase in the volume.

BRIEF DESCRIPTION OF THE FIGURES

A better understanding of the features and advantages of the present disclosure will be obtained by reference to the accompanying drawings, which are intended to illustrate, not limit, the present teachings.

FIGS. 6A, 6B, and 6C illustrate various configurations of volumes for positioning a plurality of targets according to various embodiments of the present teachings;

DETAILED DESCRIPTION

To provide a more thorough understanding of the present invention, the following description sets forth numerous specific details, such as specific configurations, parameters, examples, and the like. It should be recognized, however, that such description is not intended as a limitation on the scope of the present invention, but is intended to provide a better description of the exemplary embodiments.

The present application relates to methods and systems for aligning and positioning desired targets in fluid. Aligning or sorting desired samples, particles, objects or other targets in a fluid has been a challenge. Often, the desired targets are included in a large volume making efficient and fast extraction or analysis, for example, difficult. According to various embodiments described herein, methods and systems of aligning a plurality of targets in a flat-field configuration for extraction, sorting, or imaging in a single field of view are provided.

The generation of the plurality of targets and examples of applications using a flat-field imaging system are described in provisional applications 61/470,713, filed on Apr. 1, 2011, and 61/481,085, filed on Apr. 29, 2011, both entitled System And Method For Determining Copies-Per-Unit-Volume Using PCR And Flow Control Of Droplets, and both of which are incorporated herein by reference in their entirety.

Figure 1:
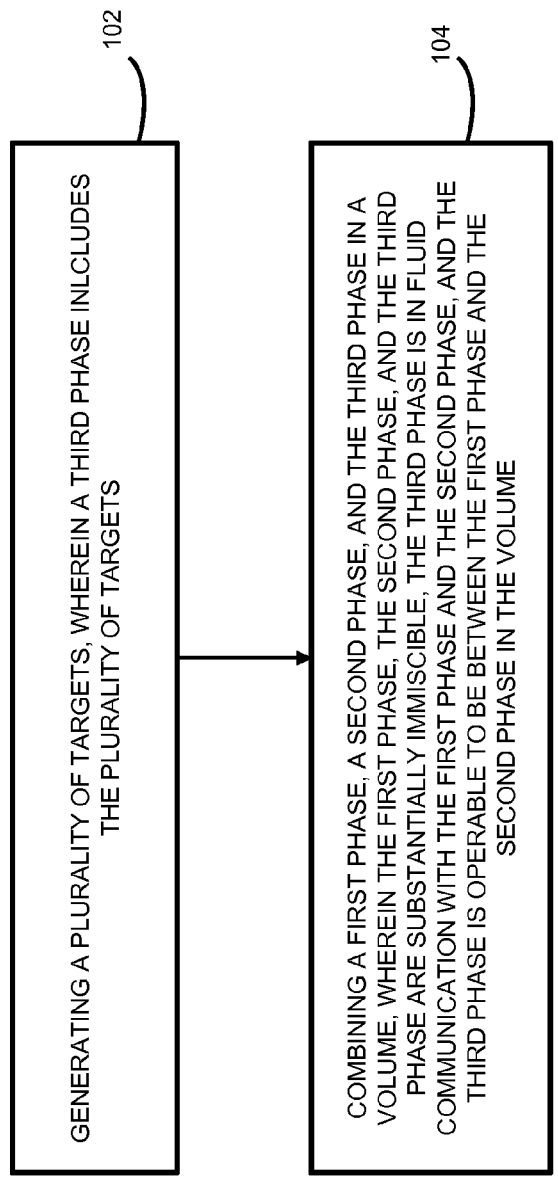
FIG. 1 is an exemplary flowchart of a method for positioning a plurality of targets according to various embodiments of the present teachings.

FIG. 1 illustrates a method of aligning a plurality of targets in fluid according to various embodiments described herein. In step 102, a plurality of targets is generated. The plurality of targets may be included in a third phase. The plurality of targets may be an emulsion, porous beads, or hollow beads, among other things for example. In some embodiments, the plurality of targets may contain a biological sample.

In various embodiments, the plurality of targets may initially be in the other phases. However, after some settlement of the at least three phases, the plurality of targets will congregate within the third phase. Furthermore, in some embodiments, the plurality of targets may have a similar density as the first or second phases. In yet other embodiments, the plurality of targets may have densities similar to the first, second and third phase. In these situations, sorting of the plurality of targets may be possible since the targets with densities corresponding to the density of a phase will eventually settle within that phase.

In step 104, a first phase, a second phase, and the third phase, including the plurality of targets, are combined in a volume. According to embodiments described herein, a volume may be a volume of phases. A phase may be a fluid, such as a liquid, that surrounds the targets. In various embodiments, the volume may include two or more different phases.

The first phase, the second phase, and the third phase are substantially immiscible with each other. According to embodiments described herein, the two or more phases, or fluids, may have different densities, viscosities, interfacial tension, laminar flow for a flowing system, or any other suitable property which prevents two adjacent liquids from mixing. In embodiments of the teachings described herein, substantially immiscible means up to 50% of a phase remains unmixed with another phase. In other words, substantially immiscible also is defined as up to 50% of the phase may be mixed with another phase. The amount of a phase that mixes with another phase may depend on the density of the phases, for example, as well as other characteristics. In other embodiments, the volume may include a fluid having a non-uniform density.

Figure 3:
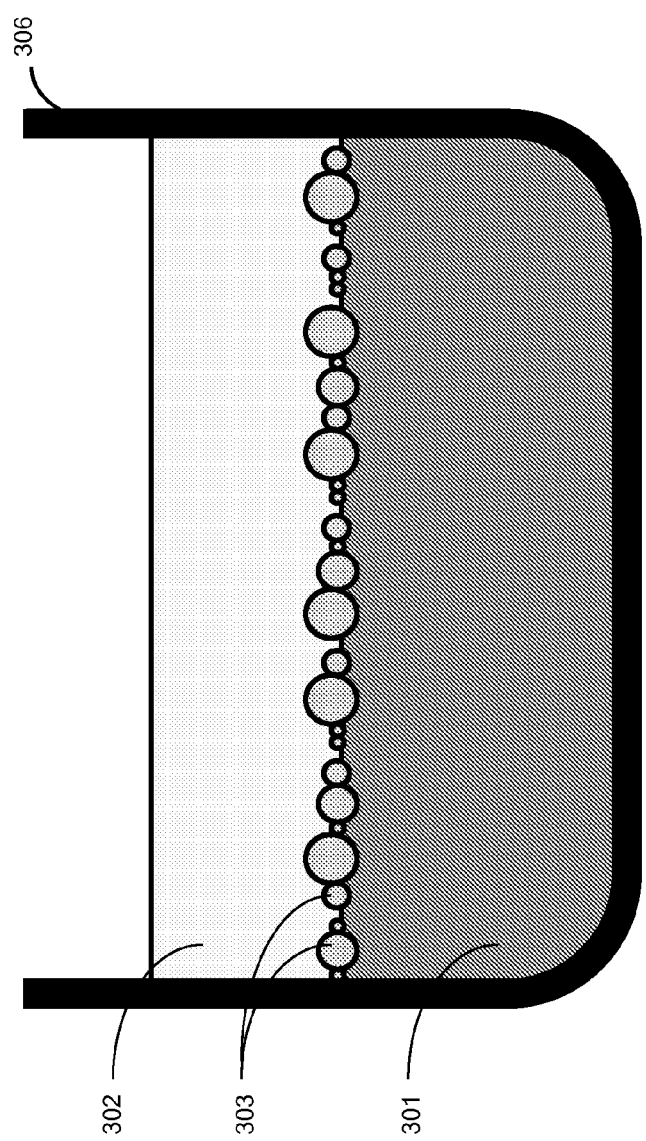
FIG. 3 illustrates a cross-section of a volume for aligning a plurality of targets according to various embodiments of the present teachings.

Further, within the volume, the third phase is in fluid communication with the first phase and the second phase. The third phase, including the plurality of targets, is operable to be positioned between the first phase and the second phase. As such, the plurality of targets is within the layer of the third phase between the first phase and the second phase. In this way, the targets are positioned so they are grouped together within the volume. A volume according to various embodiments is illustrated in FIG. 3 and will be described in more detail below.

In some embodiments, the plurality of targets may be positioned to be in a flat-field configuration so that the targets are within the field of view of an optical sensor, as described in more detail below. An optical sensor may be a camera, such as a CMOS or CCD camera, PMT, or any other optical sensing technology, for example. The optical sensor may be in a scanning flat-bed configuration, for example. In other embodiments, the plurality of targets are sorted or extracted in a more rapid manner than previous methods.

Imaging

To improve accuracy and quality of an image, the targets desired to be imaged should be in the field of view of the optical sensor. Furthermore, a more successful image of targets in a fluid will have as many of the targets in focus and have as very little overlap of the targets in the image. Thus, the improved systems and methods for aligning and positioning targets described herein may be used for an improved imaging system.

According to embodiments described herein, targets are objects within the imaging volume that are desired to be imaged. Targets may be droplets, hollow beads, magnetic beads, or any other object which is desired to be imaged. A goal for imaging the targets, for example, is to optically measure properties of the targets. Properties that may be measured from the image are the size and/or volume of the targets, fluorescence emissions from the target either at a single wavelength or multiple wavelengths, turbidity, optical density, or any other suitable detection characteristic, for example.

Figure 2:
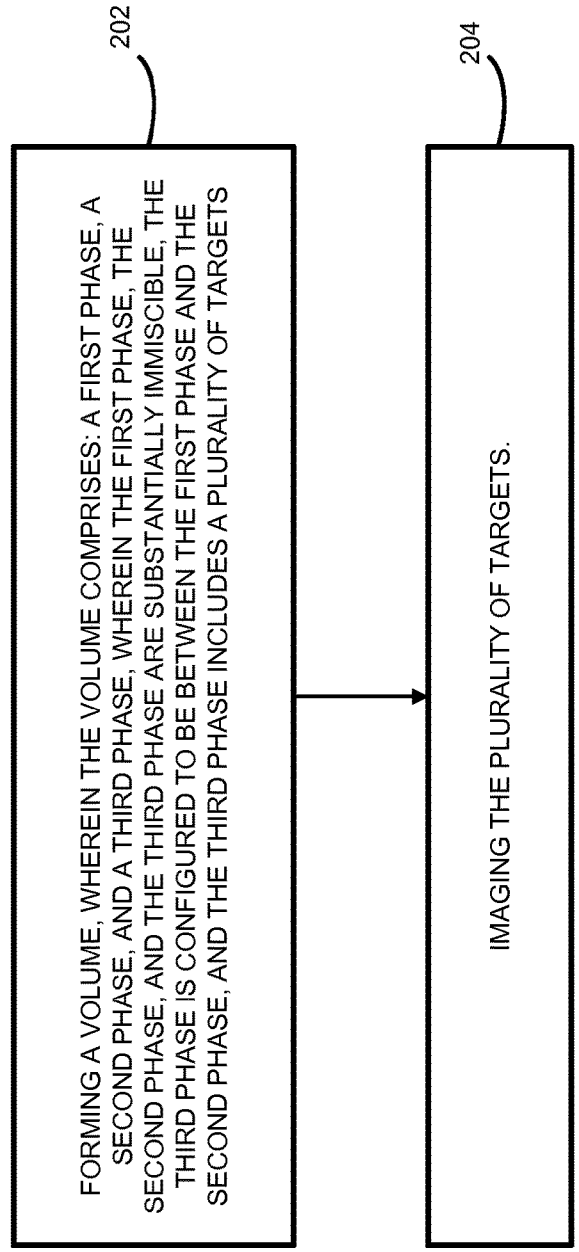
FIG. 2 is an exemplary flowchart of a method for positioning a plurality of targets according to various embodiments of the present teachings.

FIG. 2 is a flowchart illustrating an exemplary method according to embodiments of the present teachings. The method includes, in step 202, forming a volume. The volume includes a first phase, a second phase, and a third phase. In various embodiments, the first phase and second phase are different fluids, and the third phase comprises the targets. These three phases are substantially immiscible. The third phase may have properties such that it is positioned between the first phase and the second phase. The third phase may then be within a field of view of an optical sensor. The method further may include, in step 204, imaging the plurality of targets. In other words, the third phase, including the targets, may be positioned above the first phase and below the second phase. Further, the targets may be imaged in focus since the targets are within the field of view of a camera.

The side-view cross-section of an exemplary volume is illustrated in FIG. 3. A first phase 301 is depicted below a second phase 302. Between the first phase 301 and the second phase 302, is a third phase comprising targets 303. Here, the first phase 301 has a higher density than both the second phase 302 and third phase, including targets 303. The third phase, including the targets 303, has a higher density than the second phase 302. The volume may be contained in vessel 306.

In certain embodiments, the viscosity of phases affects the stability of the targets in the third phase. For example, a second phase that is more viscous than the first phase may improve the stability of the plurality of targets within the third phase.

In some embodiments, the third phase 303 may include the targets. In this configuration shown in FIG. 3 according to various embodiments, the targets are captured in a location between the first phase 301 and the second phase 302. The first phase 301 may be a liquid such as a fluorinated fluid (HFE), or a mixture of different fluorinated fluids, for example. The second phase 302 maybe a mineral oil, for example. Mineral oil does not dissolve in a fluorinated fluid.

Targets 303 of the third phase may be, but are not limited to, droplets, and non-magnetic beads, including porous beads, or hollow beads, for example. The droplets may be an emulsion. The porous or hollow beads may be spherical or cylindrical. The targets may comprise a passive reference dye, a light-scattering enhancing material, q-dots, a protein, a colloidal metal, colloidal gold, a reporter dye, a reaction-independent flow marker, or a combination thereof. In some embodiments, each of the plurality of targets is a discrete sample portion. The plurality of targets may comprise a primer pair, a nucleotide probe, a Taq polymerase, or a single cell, among other things or any other suitable particle for capture in a droplet, for example.

Second phase 302 prevents evaporation of the third phase and the first phase 301. The second phase 302 on top of the targets may help to reduce breakage of the droplets, if the droplets are an emulsion according to some embodiments. Furthermore, second phase 302 may help reduce the overlapping of the targets 303 between the first phase 301 and the second phase 302. Second phase 302 may also help reduce the motion of the droplets because of the viscosity of the second phase.

Figure 4:
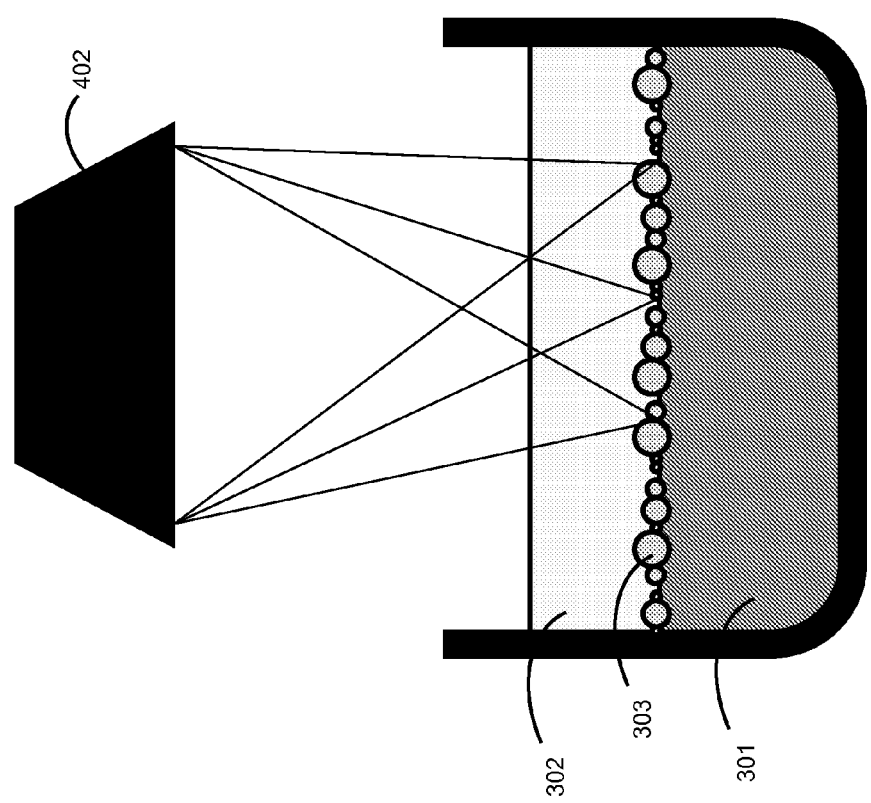
FIG. 4 illustrates an imaging system according to various embodiments of the present teachings.

An exemplary imaging system is depicted in FIG. 4. The volume, as in FIG. 3, comprises a first phase 301 on the bottom of the volume. A third phase including targets 303 is held in between a top second phase 302. As such, the targets 303 are in a substantially flattened configuration. Targets are configured such that they are within the field of view, or the focal plane, of an optical sensor 402. As mentioned above, an optical sensor may be a camera, such as a CMOS or CCD camera, PMT, or any other optical sensing technology, for example. The optical sensor may be in a scanning flat-bed configuration, for example. Any standard light source may also be used in the imaging system. For example, the light source may be a laser or LED, in some embodiments. The lighting configuration may also be reflective or passthrough. The depth of focus includes the targets 303. The image taken with optical sensor 402 may include most or all of the targets 303 in focus so that a more complete and accurate analysis may be performed. The optical sensor may be positioned above or below the volume to image the plurality of targets. In other embodiments, the optical sensor may be a scanning optical sensor, similar to a flatbed scanning system.

Examples of Applications

In various embodiments, images taken in accordance with the embodiments described herein may be analyzed to identify and quantify individual proteins, nucleic acids, or other species that constitute the solutes. The flat-field configuration for a plurality of targets according to embodiments described in this document may be used in applications involving image analysis, extraction, or sorting of targets, for example, but are not limited to these applications.

For example, in various embodiments, the methods and systems described herein may be used to detect other biological components of interest. These biological components of interest may be any suitable biological target including, but are not limited to, DNA sequences (including cell-free DNA), RNA sequences, genes, oligonucleotides, molecules, proteins, biomarkers, cells (e.g., circulating tumor cells), or any other suitable target biomolecule.

In various embodiments, such biological components may be used in conjunction with various PCR, qPCR, and/or dPCR methods and systems in applications such as fetal diagnostics, multiplex dPCR, viral detection and quantification standards, genotyping, sequencing validation, mutation detection, detection of genetically modified organisms, rare allele detection, and copy number variation.

Furthermore, as used herein, thermal cycling may include using a thermal cycler, isothermal amplification, thermal convention, infrared mediated thermal cycling, or helicase dependent amplification, for example. In some embodiments, the chip may be integrated with a built-in heating element.

According to various embodiments, detection of a target may be, but is not limited to, fluorescence detection, detection of positive or negative ions, pH detection, voltage detection, or current detection, alone or in combination, for example.

In one example, a plurality of targets according to various embodiments may be used in digital Polymerase Chain Reaction (dPCR). DPCR is a method that has been described, for example, in U.S. Pat. No. 6,143,496 to Brown et al. Results from dPCR can be used to detect and quantify the concentration of rare alleles, to provide absolute quantitation of nucleic acid samples, and to measure low fold-changes in nucleic acid concentration.

dPCR is often performed using an apparatus adapted from conventional qPCR, in which replicates are arrayed in a two dimensional array format including m rows by n columns, i.e., an m×n format. PCR cycling and read-out (end-point or real-time) generally occurs within the same array. A maximum of m×n replicates can be processed in a single batch run. Generally, increasing the number of replicates increases the accuracy, precision, and reproducibility of dPCR results.

The (m×n) format in most quantitative polymerase chain reaction (qPCR) platforms is designed for sample-by-assay experiments, in which PCR results need to be addressable for post-run analysis. For dPCR, however, the specific position or well of each PCR result may be immaterial and only the number of positive and negative replicates per sample may be analyzed.

The read-out of dPCR, that is, the number of positive reactions and the number of negative reactions, may be used to calculate starting template concentration based on a Poisson equation, as follows:

$$f(k; \lambda) = \frac{\lambda^k e^{-\lambda}}{k!}.$$

On the other hand, the read-out of qPCR (signal vs. cycle) is proportional to the log of the template concentration. For this reason, dPCR typically is constrained to a narrow dynamic range of template input.

According to various embodiments, a dPCR analysis of a sample may include preparing and analyzing uniform or variously-sized targets. These targets may be sample portions, such as poly dispersed or multi-mono dispersed emulsions.

Multi-mono dispersed emulsions, also referred to as poly-dispersed emulsions, are less difficult to make, minimally handled, can be formed in batches, and greatly increase the dynamic range of dPCR. Furthermore, a small reaction chambers may allow analysis without sample dilution that can introduce error. For example, heat, shaking, sonic energy, ultrasonic baths, combinations thereof, and the like can be used to produce emulsions, for example, to process batches of emulsions in 96-well, 384-well plates, or cell culture plates without the need for any special consumables to physically touch the samples. In other embodiments, a plate may be used based on the amplification apparatus. This greatly reduces the chance of cross-contamination. In addition, multi-mono dispersed emulsions may typically vary in volume on the order of 1 fL to 50 μL. In some embodiments, multi-mono dispersed emulsions may vary in volume from about 1 pL to 500 pL, eliminating the need to dilute samples to achieve terminal dilutions.

As mentioned above, multi-mono dispersed emulsions may be imaged and analyzed according to various embodiments. A multi-mono dispersed emulsion may include two or more sizes of targets, where the sizes are known or predetermined. For example, a multi-mono dispersed emulsion may contain three different sizes of targets that are substantially the same size as three different predetermined sizes. Substantially the same size means within +/−10% of the predetermined size. By determining which size of the different predetermined sizes each discrete sample portion is, the volume of each discrete sample portion can then be determined. Multi-mono dispersed emulsions may vary in volume from about 1 fL to 10 pL. In other words, each droplet can be binned into a predetermined size. In this way, the dynamic range can be increased and analysis of an image may be simplified.

The sample portions are amplified so that the sample portions contain the target nucleic acid. Amplification may be performed by polymerase chain reactions (PCR) with target concentration near terminal dilution. The volume of the sample portions may be known. If the sample portions are different sizes, the volume of the sample portions may need to be determined. The positive and negative reactions within the plurality of sample portions are counted. More particularly, the number of sample portions that contain successful amplification of the target nucleic acid are counted. The sizes and the positive and negative reactions may be determined by imaging the sample portions, as targets, according to embodiments of the present teachings, for example. The average copy number per reaction is estimated. The estimation may be made using a Poisson distribution. Then, the target copy number per unit volume in the starting sample is estimated.

As described above, an image generated by various embodiments may be used to estimate the volume of the plurality of targets, for dPCR analysis.

The image generating according to various embodiments may be used to compare the plurality of amplified sample portions, the targets, to a plurality of standards of known respective volumes, for example, a plurality of standards of known respective volume that uniformly sized or that are of different known volumes. Analysis of the image may further comprise subjecting a plurality of portions of a standard to the same nucleic acid amplification conditions to form a plurality of processed standards, wherein each of the processed standards are of a known respective volume, and then comparing the image of the plurality of processed standards to the plurality of processed sample portions. In some embodiments, the plurality of sample portions have an average of from about 0.1 to about 0.8 copy of the target nucleic acid per discrete loaded mixture. The plurality of sample portions may have an average diameter of from about 0.3 micrometer (μm) to about 600 μm, or an average diameter of from about 1.0 μm to about 100 μm, or an average volume of from about 0.5 femtoliter (fL) to about 1 microliter (μL), or an average volume of from about 10.0 fL to about 100 nanoliters (nL). However, in some embodiments, a sample portion may be as large as 65 pL.

In an example of image analysis of an image generated by embodiments of the present teachings, sample portions of first, second, and third volumes of different known respective standard sizes may contain first, second, and third respective detectably unique dyes and may be identified and used to scale the size of the discrete sample portions having unknown volume sizes. Sample portion may be generated with sizes of from about 0.3 μm in diameter up to about 1000 μm in diameter, for example, from about 0.4 μm in diameter up to about 300 μm in diameter, from about 0.5 μm in diameter up to about 200 μm in diameter, or from about 1.0 μm in diameter up to about 100 μm in diameter. Sample portion volumes are of up to about 1.0 μL in size may be produced and processed. Sample portion volumes based on spherical diameters measured through image analysis can be estimated, for example, using a conversion chart such as this one:

| Radius | diameter | volume | |
|---|---|---|---|
| 0.6 uM | 1.2 uM | 1 fL | e. coli |
| 1.4 uM | 2.8 uM | 10 fL | |
| 3 uM | 6 uM | 100 fL | |
| 6 uM | 12 uM | 1 pL | |
| 14 uM | 28 uM | 10 pL | human cell |
| 30 uM | 60 uM | 100 pL | |
| 60 uM | 120 uM | 1 nL | |
| 140 uM | 280 uM | 10 nL | |

-continued

| Radius | diameter | volume |
|---|---|---|
| 300 uM | 600 uM | 100 nL |
| 600 uM | 1200 uM | 1 uL |

Measuring the size of each of the plurality of processed sample portions may comprise analyzing each of the plurality of processed sample portions, and the analyzing may comprise one or more of measuring or analyzing an index of refraction, a light scattering property, a forward light scattering property, a side light scattering property, an optical absorption property, an optical transmission property, a peak height of an optical signal, a peak width of an optical signal, a fluorescent property, a time-of-flight fluorescent property, or a combination thereof. The method may further comprise estimating what size of processed sample portion provides a specific percentage of processed sample portions of that size that test positive for the presence of one or more of the at least one target nucleic acid, or estimating what size processed sample portion of the differently-sized processed sample portions provides a 50% positivity rate with regard to determining the presence of one or more of the at least one target nucleic acid.

In various embodiments, the methods and systems described herein may be used to detect other biological components of interest. These biological components of interest may include, but are not limited to, cells and circulating tumor cells, for example. Furthermore, in addition to dPCR, the methods and systems in various embodiments may be used in applications, such as fetal diagnostics, multiplex DPCR, viral detection, genotyping, and rare allele detection copy number variation.

Generation of the Plurality of Targets

According to various embodiments, the targets may also be generated. An emulsion apparatus may generate a plurality of targets. The emulsion apparatus may generate the plurality of targets by various methods, such as shaking, stirring, sonicating, extruding, or electrowetting, for example. In some embodiments, the emulsion apparatus may be a sonicator, a vortexer, or a plate shaker. In other embodiments, magnetic beads may be used to stir a third phase to generate the plurality of targets. Emulsification parameters, such as emulsification method, strength/power, time, oil/surfactant chemistry, viscosity, concentration, aqueous phase composition, and water-to-oil ratio, for example, may be optimized to produce desired sizes for the targets. In some embodiments, the targets have a diameter of between 10μ, to 150 μm and a volume of between 1 pL to 1 nL.

Exemplary systems for methods of preparing and processing emulsions that may be used according to the present teachings include those described in U.S. patent application Ser. No. 12/756,547, filed Apr. 8, 2010, to Lau et al. for "System and method for preparing and using bulk emulsion," which is incorporated herein in its entirety by reference. Exemplary systems for methods of processing and thermally cycling emulsions that may be used according to the present teachings include those described in U.S. patent application Ser. No. 12/756,783, filed Apr. 8, 2010, to Liu et al. for "System comprising dual-sided thermal cycler and emulsion PCR in a pouch," which is also incorporated herein in its entirety by reference.

Generating the targets may also include diluting the sample to form a diluted sample and forming the plurality of targets from the diluted sample. Dilution may comprise terminally diluting the sample to achieve an average of less than one of the at least one target nucleic acid molecules per imaging target. In some embodiments, the method further comprises: serially diluting different portions of the sample by different respective dilution ratios; dividing each serially diluted portion into a plurality of aliquots; and processing each of the plurality of aliquots of each of the serially diluted portions.

According to various embodiments, the components of the plurality of targets may be provided in a multi-well plate. Forming the plurality of targets may include emulsifying an aqueous sample with a medium that is at least substantially immiscible with the sample. In some embodiments, the emulsifying may comprise mixing the aqueous sample with the medium that is at least substantially immiscible with the sample in the multi-well plate, sonicating the aqueous sample with the medium that is at least substantially immiscible with the sample in the multi-well plate, shaking the aqueous sample in the medium that is at least substantially immiscible with the sample in the multi-well plate, or stirring the aqueous sample in the medium that is at least substantially immiscible with the sample in the multi-well plate. According to various embodiments, surfactant may be added to a phase to generate the plurality of targets, or discrete sample portions. The quality of the plurality of targets that are generated may depend on the components of the phases. For example, the second phase containing a surfactant may make a plurality of targets with good integrity in the third phase including certain components.

According to various embodiments, imaging target stability is a relevant factor. Stability ensures that the targets when in proximity to each other, the targets do not coalesce. Very stable emulsions allow very high density of targets since targets can "touch" each other while maintaining a minimal layer of oil in between. As such, emulsification to form a plurality of targets may also take place in the presence of a surfactant, so that the kinetic stability of the emulsion increases. These surfactants then line the surface of the targets, stabilizing it. Some surfactants which may be used, but are not limited to, are Span80, STF9, ABIL EM90, KRYTOX, and DC BY11-030, for example.

Any of a variety of substantially or totally immiscible fluids can be used as the carrier fluid. Immiscibility is determined with respect to the aqueous sample droplets, the targets. The substantially or totally immiscible fluid may comprise, for example, paraffin oil, mineral oil, silicone oil, a perfluorinated polyether (PFPE), other fluorinated fluids, fluorinated solvents, combinations thereof, and the like. Some specific fluids that can be used as a carrier fluids include GALDEN® HT170 available from SOLVAY SOLEXIS of West Deptford, N.J., other GALDEN® HT liquids available from SOLVAY SOLEXIS, FC-40 available from 3M Company of St. Paul, Minn., and other FLUORINERT™ liquids available from 3M Company of St. Paul, Minn.

Generating Targets in the Presence of the First and Second Phases

Figure 5:
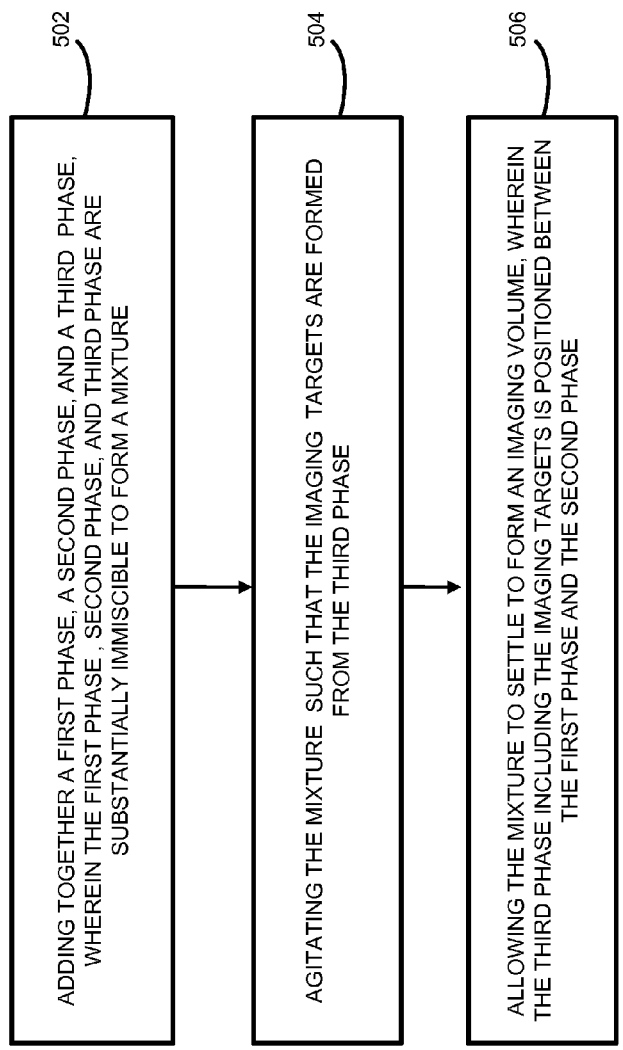
FIG. 5 is an exemplary flowchart of a method for forming targets according to various embodiments of the present teachings.

According to various embodiments, emulsification to form the plurality of targets may be in the presence of the first phase and the second phase. In some embodiments of the present teachings, the plurality of targets may be generated in the volume in the presence of the first and second phases. In other embodiments, the plurality of targets may be generated outside the volume in a vessel and added to the volume already containing the first phase and the second phase. An exemplary method to form the targets in the presence of the first phase and the second phase is shown in FIG. 5.

In step 502, a first phase, a second phase, and a third phase are added together to form a mixture. The first phase, the second phase, and third phase are substantially immiscible. The mixture may contain surfactant. The third phase may comprise, in certain embodiments, the sample as described above. The mixture is agitated in step 504 to form a plurality of targets. The agitation may be from shaking, stirring, sonicating, extruding, or electowetting, for example. In general, there is a relationship between the energy of agitation and the size distribution of the plurality of targets. For example, higher energy agitation may generate smaller-sized targets. As described above, the targets may be droplets of various sizes, a multi-mono dispersed emulsion (polydispersed emulsion), or of two or more known sizes, a multi-mono dispersed emulsion. In step 506, the mixture is allowed to rest and settle so that the three phases separate, according to densities of the phases, to form an imaging volume. The targets settle into position between the first phase and the second phase.

Meniscus of the Third Phase

As mentioned above, the volume may be contained in a vessel 306. In order to improve an image taken according to embodiments of the present teachings, the meniscus of the first phase and second phase may be considered. A meniscus may cause the third phase including the targets to be convex or concave with respect to the optical sensor and affect the quality of an image.

An exemplary imaging volume 602 is depicted in FIG. 6A. The interface between the phases is flat. In this case, the targets are dispersed substantially evenly in the field of view of the optical sensor. The generated image will have more targets in better focus and prevent overlapping of the targets so that more targets may be imaged for analysis.

FIG. 6B illustrates another exemplary imaging volume 604 with a meniscus that creates a concave third phase with respect to an optical sensor positioned above the imaging volume 604. In this case, the meniscus could force aggregation of targets toward the center of the third phase layer to a point when the targets overlap. Also, because of the concave shape of the third phase, the depth of field may not be wide enough to image the targets in focus at all points. On the other hand, convex meniscus, with respect to a above-positioned optical sensor, as illustrated in FIG. 6C, may cause targets to be dragged to the edge of the vessel 306 and away from the center, which would result in reduced number of accurately imaged targets.

Thus, according to various embodiments, vessel walls may be coated with a material to modify the meniscus. The coating may include a variety of hydrophobic materials. For example, the interior walls of the vessel 306, containing an imaging volume, may be coated with Teflon. In other embodiments, the shape of the vessel well may modify the meniscus angle. For example, the vessel 306 may have a well in a cone or inverted cone shape that would flatten out the meniscus angle. In other embodiments, the viscosity of the phases may be considered for minimizing the meniscus angle.

In other embodiments, convex meniscus may be tolerated by overloading or preloading the meniscus with excess targets. These excess targets may not be of interest for analyzing. In other words, there may not be any sample within the targets that need to be analyzed by imaging, for example. In this way, overlapping of targets of interest, i.e., targets containing sample, will be minimized and analysis may be more accurate.

Furthermore, in other embodiments, viscosity of the first phase or the second phase may alleviate some issues related to the meniscus described above. More viscous oils may be used, in some embodiments, to limit target movement and limit target migration towards the edges of the vessel.

However, in some embodiments, the meniscus allows the smaller targets to gather near the meniscus, while the larger targets remain closer to the center of the third phase. As such, within the third phase, there may be sorting of the smaller-sized targets because the larger-sized targets would stay closer to the middle of the third phase while the smaller-sized targets move toward the vessel wall and meniscus. In some embodiments, magnetic beads may be in the third phase and be used to agitate the third phase to assist with the sorting process.

Overlapping of Targets

Figure 7A:
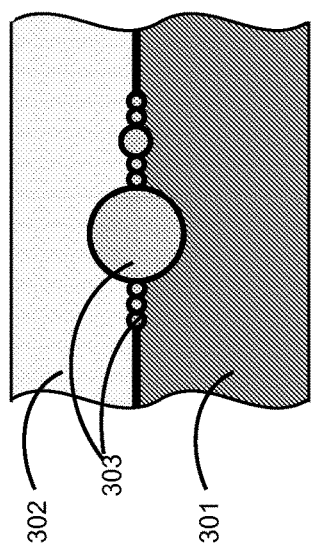
FIGS. 7A, 7B, and 7C illustrate various configurations of volumes for positioning a plurality of targets according to various embodiments of the present teachings.
Figure 7C:
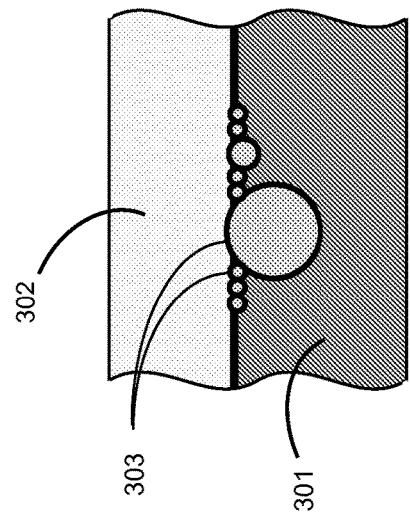
Figure 7B:
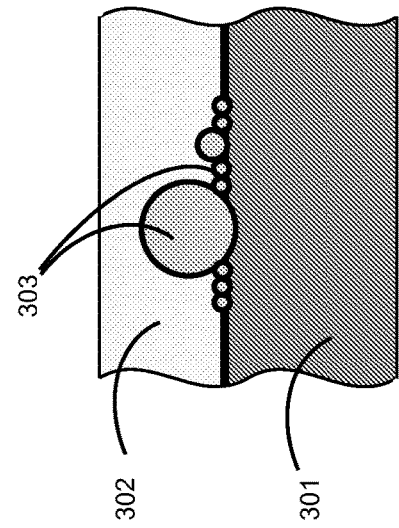

As described above, multi-mono dispersed emulsions may comprise targets of a plurality of sizes. In the embodiment depicted in FIG. 7A, the targets 303 are positioned between the first phase 301 and the second phase 302 such that the targets 303 have minimal overlap. However, as illustrated in FIG. 7B, there is overlap in targets 303. In particular, smaller targets may be covered by an edge of a larger imaging target. In another example, targets 303 may have a density closer to the first phase 301, pulling larger imaging droplets lower. In this case, targets may not be accurately imaged.

In various embodiments, overlapping may be reduced by forming a volume in which the third phase has a density of about the average of the densities of the first phase and the second phase.

In other embodiments, the overlapping may be reduced by forming a volume with a first phase, second phase, and third phase, having densities that are very close. In yet other embodiments, overlapping may be alleviated by the first and second phases having densities far from the density of the third phase.

In some embodiments, the third phase including the targets is diluted. In this way, the targets are spread out enough in the focal layer that the overlap events are more infrequent.

In yet other embodiments, there may be a small volume of the first phase in the vessel. In other words, the depth of the first phase in the vessel may be small enough that the larger targets, included in the third phase, may rest on the bottom of the vessel. As such, the friction between the targets that contact the bottom surface of the vessel may tend to not have as much motion. Thus, this may provide more stability to the planar flat-field configuration in the third phase. Additionally, since the larger targets may tend to have less movement than the smaller targets not in contact with the bottom surface of the vessel, this may be useful for sorting the plurality of targets by size.

On the other hand, in mono dispersed emulsions, when the targets are all substantially the same size, there may be no physical space for the targets to overlap with each other.

Figure 8:
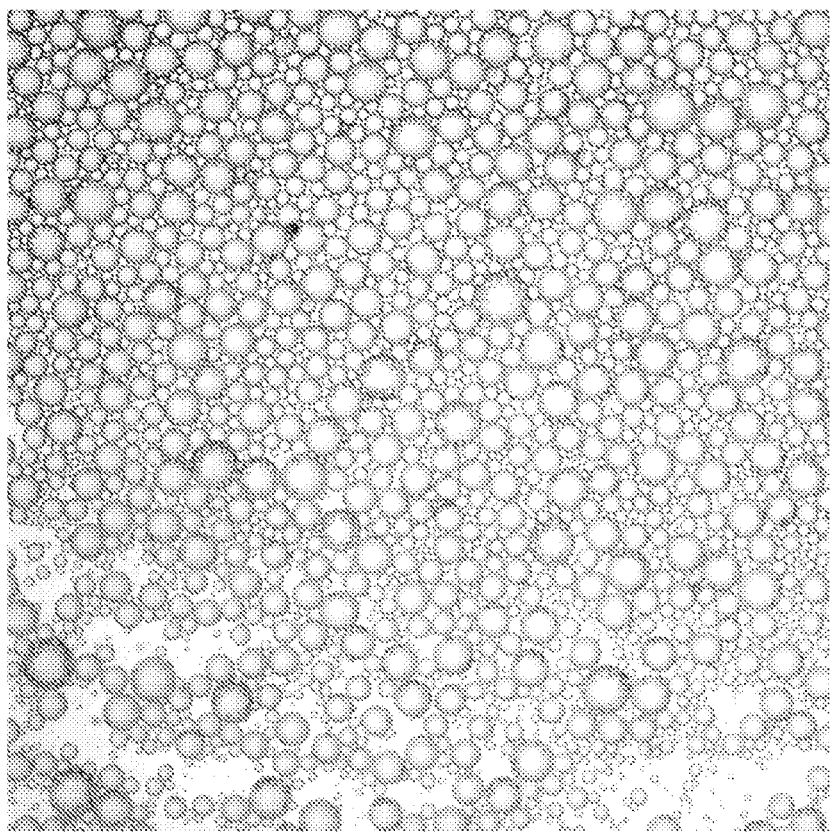
FIG. 8 illustrates an exemplary image taken of the positioned plurality of targets according to various embodiments of the present teachings.

FIG. 8 illustrates an exemplary image of a plurality of targets taken in accordance with embodiments and methods described herein. The image shown in FIG. 8 illustrates a white light image taken of a plurality of targets.

Figure 9:
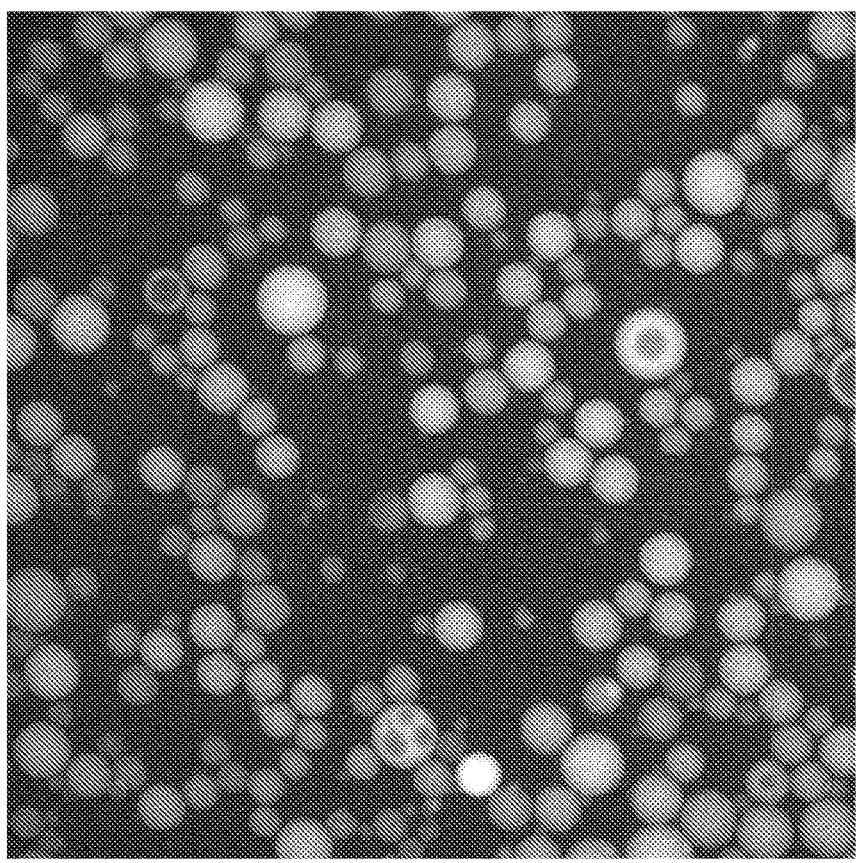
FIG. 9 illustrates another exemplary image taken of the positioned plurality of targets according to various embodiments of the present teachings.

FIG. 9 illustrates another exemplary image of a plurality of targets taken in accordance with embodiments and methods described herein. In this example, the targets are droplets containing samples amplified by PCR. Successful PCR reactions can be identified in this image from the fluorescent emissions from some of droplets of the plurality of droplets imaged.

Although the present invention has been described with respect to certain exemplary embodiments, examples, and applications, it will be apparent to those skilled in the art that various modifications and changes may be made without departing from the invention.

What is claimed is:

1. A method for imaging droplets comprising biological component or sample, the method comprising:
   forming a volume, wherein the volume comprises:
   a first phase,
   a second phase, and
   a third phase, wherein:
     the first phase, the second phase, and the third phase are substantially immiscible,
     the third phase is in fluid communication with the first phase and the second phase and is within a field of view of an optical sensor, and
     the third phase includes a plurality of droplets comprising biological component or sample; and
   simultaneously imaging, using an optical sensor, the plurality of droplets, wherein the plurality of droplets are disposed in a substantially non-overlapping single layer within the volume during the imaging.

2. The method of claim 1, wherein the first phase has a first density, the second phase has a second density, and the third phase as a third density, wherein first density is heavier than the third density and the third density is heavier than the second density.

3. The method of claim 2, wherein the first phase is positioned below the third phase and the third phase is positioned below the second phase.

4. The method of claim 2, wherein the plurality of droplets have substantially the same density as the third density.

5. The method of claim 1, wherein the first phase comprises a fluorinated fluid (HFE), and the second phase comprises a mineral oil.

6. The method of claim 1, wherein the plurality of droplets comprises droplets of a plurality of sizes.

7. A system for imaging droplets comprising biological component or sample, the system comprising:
   a volume, wherein the volume comprises:
   a first phase,
   a second phase, and
   a third phase, wherein:
     the first phase, the second phase, and the third phase are substantially immiscible,
     the third phase is configured to be positioned between the first phase and the second phase, and
     the third phase includes a plurality of droplets comprising biological component or sample, the plurality of droplets being disposed in a substantially non-overlapping single layer within the volume; and
   an optical sensor having a field of view including the third phase for simultaneously imaging the plurality of droplets in the volume.

8. The system of claim 7, wherein the volume is contained in a vessel.

9. The system of claim 7, wherein the optical sensor is positioned above the volume.

10. The system of claim 7, wherein the optical sensor is positioned below the volume.

11. The system of claim 7, wherein the first phase has a first density, the second phase has a second density, and the third phase as a third density, wherein first density is heavier than the third density and the third density is heavier than the second density.

12. The system of claim 11, wherein the first phase is positioned below the third phase and the third phase is positioned below the second phase.

13. The system of claim 11, wherein the plurality of droplets have substantially the same density as the third density.

14. The system of claim 7, wherein the second phase comprises a fluorinated fluid (HFE), and the first phase comprises a mineral oil.

15. The system of claim 7, wherein the plurality of droplets comprises droplets of a plurality of sizes.

16. The system of claim 7, wherein the third phase further includes a medium that is at least substantially immiscible with the plurality of droplets.

17. The system of claim 16, wherein the medium that is substantially immiscible with the plurality of droplets comprises at least one selected from the group consisting of: a mineral oil, a silicone oil, a paraffin oil, a fluorinated fluid, a perfluorinated polyether.

18. The system of claim 7, wherein at least some of the plurality of droplets contain a porous beads.

19. The system of claim 7, wherein the plurality of droplets comprises magnetic beads.

* * * * *